United States Patent [19]

Watanabe et al.

[11] Patent Number: 5,212,311
[45] Date of Patent: May 18, 1993

[54] CHIRAL AMINO-METHYL FERROCENE DERIVATIVES

[75] Inventors: Makoto Watanabe; Masaru Uemura, both of Yokkaichi; Shuki Araki; Yasuo Butsugan, both of Nagoya, all of Japan

[73] Assignee: Tosoh Corporation, Yamaguchi, Japan

[21] Appl. No.: 772,455

[22] Filed: Oct. 7, 1991

Related U.S. Application Data

[63] Continuation of Ser. No. 490,408, Mar. 8, 1990, Pat. No. 5,079,359.

[30] Foreign Application Priority Data

Mar. 9, 1989 [JP] Japan ..................................... 1-57232
Sep. 25, 1989 [JP] Japan ..................................... 1-249869

[51] Int. Cl.$^5$ ............................................. C07F 17/12
[52] U.S. Cl. .......................................... 546/11; 546/2; 540/541; 548/402; 556/144
[58] Field of Search ...................... 546/2, 11; 556/144; 548/402; 544/64; 540/541

[56] References Cited

PUBLICATIONS

*Journal of Amer. Chem. Soc., 92:18, Sep. 9, 1970,* "Correlation of Central and Planar Chirality in Ferrocene Derivatives", Dieter Marquarding et al., pp. 5389–5393.
"Derivatives of Dicyclopentadienyliron", F. S. Arimoto et al., pp. JACS 77, 6295–6297 (1955).
*J. Org. Chem.,* vol. 37, No. 20, 1972. "The Retentive Nucleophilic Displacements of α-Substituted Alkylferrocenes", George W. Gokel et al., pp. 3052–3058.
*Tetrahedron,* vol. 26, "Asymmetric Lithiation of Ferrocenes", T. Aratani et al., pp. 5453–5464.
*Liebigs Ann. Chem.,* 1986, "Chirale α-Ferrocenylalkylamine", Rudolf Herrmann et al., pp. 251–268.
Chemica Scripta, 1975, vol. 7, "The Chemistry of α-Ferrocenylcarbenium Tetrafluoroborates", Stig Allenmark et al., pp. 97–101 (1975).
Journal of Am. Chem. Soc., 95:2, Jan. 24, 1973, "Absolute Configuration of a 1,2-Disubstituted Ferrocene Derivative with Planar and Central Elements of Chirality and ... ", Linda F. Battelle et al., pp. 482–486 (1973).
Jrnl. of Polymer Sci., vol. 11, 1973, "Organometallic Polymers XXV. Preparation of Polyvinylferrocene", Y. Sasaki et al., pp. 1213–1224.
The Chem. Soc. of Japan, vol. 53, No. 4, "Asymmetric Synthesis Catalyzed by Chiral Ferrocenylphosphine–Transition Metal Complexes". I. Preparation of Chiral Ferrocenylphosphines, Tamio Hayashi et al., pp. 1138–1151 (1980).
J. Org. Chem., 1988, vol. 53, "Asymmetric Synthesis Catalyzed by Chiral Ferrocenylphosphine-Transition-Metal Complexes. 5. Palladium-Catalyzed Asymmetric Allylation of Active Methine Compounds", Tamio Hayashi et al., pp. 113–120 (1988).
Tetrahedron Letters, No. 23, "Asymmetric Total Synthesis of Optically Active α-Curcumene", Kohei Tamao et al., pp. 2155–2156 (1979).

*Primary Examiner*—Mark L. Berch
*Attorney, Agent, or Firm*—Wegner, Cantor, Mueller & Player

[57] ABSTRACT

A ferrocene derivatives represented by the following formula (I):

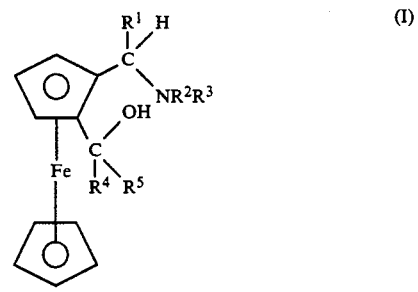

can be a useful ligand to metals with Lewis acidity and is used as a catalyst for asymmetric synthesis with good enantioselectivity. This ferrocene derivatives is synthesized from a novel haloferrocene derivative represented by formula (II) and the haloferrocene derivative is synthesized from a novel ferrocene derivative represented by formula (III).

6 Claims, No Drawings

CHIRAL AMINO-METHYL FERROCENE DERIVATIVES

This application is a continuation of Ser. No. 07/490,408, filed Mar. 8, 1990, U.S. Pat. No. 5,079,359.

BACKGROUND OF THE INVENTION

1. Field of the Invention

The present invention relates to a novel ferrocene derivative and, more in detail, an optically active ferrocene derivative as a useful catalyst for asymmetric synthesis. Further, the present invention relates to an optically active haloferrocene and ferrocene derivative.

2. Description of Prior Art

A catalyst is often used for an asymmetric synthesis method which is one of processes for preparation of an optically active substance. Examples of well-known catalysts include ephedrine and prolinol derivatives which are derived from natural sources.

Derivatives from natural sources, however, have specificity to a substrate and as a result, some substrates exhibit good enantioselectivity but the other substrates do not. Therefore, these derivatives from natural sources can not be applied to or are not suitable to many reactions.

In these circumstances, some improvement in catalysts for asymmetric synthesis derived from natural sources were attempted in order to reduce the above-mentioned specificity to a substrate and improve properties such as reaction efficiency. However, in some cases, it is not easy to change a substituent on an asymmetric carbon in the catalyst and it is impossible to obtain catalyst with desirable properties.

Ferrocenylphosphine, one of known optically active ferrocene derivatives, is used as a chiral ligand to transition metals such as palladium and rhodium. Transition metals with ferrocenylphosphine as the ligand are used as catalysts for asymmetric synthesis. (See T. Hayashi et al., Bull. Chem. Soc. Jpn., Vol.53, 1138 (1980); Tetrahedron Lett., 1979, 2155; J. Org. Chem., vol. 53, 113 (1988).) However, this catalyst can be applied only to reactions in which transition metals such as palladium and rhodium work as a catalyst, and is not applicable to a wide range of reaction.

Further, it is known that catalysts using metals with Lewis acidity such as zinc, boron, aluminum, titanium, cerium and nickel exhibit good enantioselectivity in asymmetric induction. However, no catalyst consisting of a metal with Lewis acidity to which ferrocenylphosphine is coordinated has afforded high enantioselectivity.

A provision of an optically active ferrocene derivative coordinating to a metal with Lewis acidity and exhibiting good enantioselectivity is desired.

Furthermore, aside from a metal coordination catalyst, a polymer comprising an optically active ferrocene derivative is also aspired to be provided. The polymer comprising an optically active ferrocene derivative will be used as a catalyst for heterogeneous asymmetric synthesis and a gel for an optical resolution.

An object of the present invention is to provide a novel catalyst for asymmetric synthesis which can be used instead of the above-mentioned compounds derived from natural sources.

A further object of the present invention is to provide a catalyst for asymmetric synthesis of which substituents on the asymmetric carbon are easily exchangeable.

An another object of the present invention is to provide an optically active ferrocene derivative which can be a ligand to a metal with Lewis acidity.

A further object of the present invention is to provide an optically active ferrocene derivative usable as a starting material of an optically active polymer

SUMMARY OF THE INVENTION

The present invention relates to a ferrocene derivative with chirality represented by the formula (1):

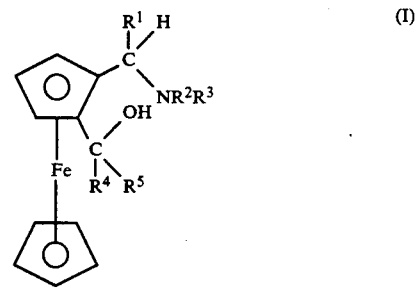

In the formula (I), $R^1$ represents an alkyl group, preferably a lower alkyl group having 1 to 6 carbon atoms. $R^2$ and $R^3$ are the same or different and represent an alkyl group, preferably a lower alkyl group having 1 to 6 carbon atoms, an aryl group, preferably a phenyl group or a benzyl group, or $R^2$ and $R^3$ form a heterocyclic ring, preferably a heterocyclic ring having 4 to 6 carbon atoms, together with a nitrogen atom to which $R^2$ and $R^3$ bond. $R^4$ and $R^5$ are the same or different and represent hydrogen, a lower alkyl group having 2 to 6 carbon atoms, an aryl group, an anthracenyl group or a ferrocenyl group, or $R^4$ and $R^5$ form a cycloalkyl group having 5 to 7 carbon atoms or a anthracenyl group together with a carbon atom to which $R^4$ and $R^5$ bond. It is provided that $R^4$ and $R^5$ are not hydrogen simultaneously, and when $R^1$, $R^2$ and $R^3$ are methyl groups, $R^4$ and $R^5$ are not phenyl groups simultaneously and are not respectively p-methoxyphenyl and hydrogen.

DETAILED DESCRIPTION OF THE INVENTION

Examples of a lower alkyl group having 1 to 6 carbon atoms represented by $R^1$, $R^2$ and $R^3$ in formula (I) include methyl, ethyl, n-propyl, iso-propyl, n-butyl, tert-butyl, n-pentyl and n-hexyl. Particularly, methyl and iso-propyl are preferred as $R^1$, and methyl, ethyl and iso-propyl are preferred as $R^2$ and $R^3$. Further examples of a heterocyclic ring which is formed with $R^2$ and $R^3$ together with a nitrogen atom to which $R^2$ and $R^3$ bond include pyrrolidine and piperidine, preferably piperidine.

Examples of a lower alkyl group having 2 to 6 carbon atoms represented by $R^4$ and $R^5$ include ethyl, n-propyl, iso-propyl, n-butyl, tert-butyl, n-pentyl and n-hexyl, preferably iso-propyl and tert-butyl. Examples of an aryl group represented by $R^4$ and $R^5$ include phenyl, o-tolyl, p-tolyl, mesityl, 2,6-dimethoxyphenyl and p-chlorophenyl. Further, examples of a cycloalkyl group which is formed with $R^4$ and $R^5$ together with a carbon atom to which $R^4$ and $R^5$ bond include cyclopentyl, cyclohexyl and cycloheptyl, preferably cyclohexyl.

Examples of the compounds of the present invention represented by formula (I) are shown in Table 1 below

TABLE 1

| No. | R¹ | R² | R³ | R⁴ | R⁵ |
|-----|----|----|----|----|----|
| 1 | Me | —N(piperidyl) | | Ph | Ph |
| 2 | Me | Me | Me | iso-Pr | iso-Pr |
| 3 | Me | Me | Me | C(cyclohexyl) | |
| 4 | Me | Et | Et | Ph | Ph |
| 5 | Me | —N(piperidyl) | | G(xanthenyl) | |
| 6 | Me | iso-Pr | iso-Pr | Ph | Ph |
| 7 | Me | Me | Me | Ph | H |
| 8 | Me | Me | Me | t-Bu | H |
| 9 | Me | —N(piperidyl) | | t-Bu | H |

Further, the present invention relates to a haloferrocene derivative represented by formula (II) and a ferrocene derivative represented by formula (III):

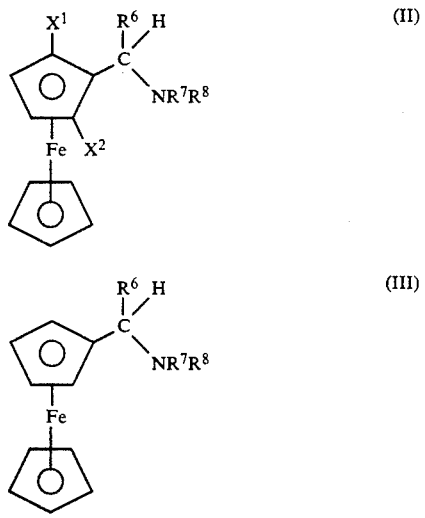

In formulas (II) and (III), $R^6$ represents hydrogen, an alkyl group, a benzyl group or an aryl group, $R^7$ and $R^8$ represent respectively hydrogen, an alkyl group, a benzyl group, an aryl group, or unsubstituted or substituted 2-hydroxyethyl group, or $R^7$ and $R^8$ can be form a heterocyclic ring together with a nitrogen atom. One of $X^1$ and $X^2$ is hydrogen and the other is halogen.

In formulas (II) and (III), an alkyl group is preferably an alkyl group having 1 to 6 carbon atoms and is exemplified by methyl, ethyl, n-propyl, iso-propyl, n-butyl, tert-butyl and n-pentyl. Examples of an aryl group include phenyl, p-tolyl, o-tolyl, p-methoxyphenyl, p-chlorophenyl, o-chlorophenyl and p-nitrophenyl. Examples of substituents of 2-hydroxyethyl group include methyl, ethyl, iso-propyl, tert-butyl, phenyl and p-tolyl.

Examples of 2-hydroxyethyl group include 2-hydroxyethyl, (R)-2-hydroxypropyl, (S)-2-hydroxypropyl, (1S,2R)-1-methyl-2-phenyl-2-hydroxyethyl, (1R,2S)-1-methyl-2-phenyl-2-hydroxyethyl, (R)-2-phenyl-2-hydroxyethyl, (S)-2-phenyl-2-hydroxyethyl, (S)-2-t-butyl-2-hydroxyethyl.

Further, examples of a heterocyclic ring which is formed with $R^7$ and $R^8$ together with a nitrogen atom to which $R^7$ and $R^8$ bond (—$NR^7R^8$) include pyrrolidyl, (S)-2-hydroxymethylpyrrolidyl, (R)-2-hydroxymethylpyrrolidyl, piperidyl, morpholyl, (S)-2-(diphenylhydroxymethyl) pyrrolidyl, (S)-2-[(S)-phenylhydroxymethyl]pyrrolidyl, (S)-2-[(R)-phenylhydroxymethyl]pyrrolidyl.

Further, examples or halogen pump include chloro, bromo and iodo.

It is preferred that the haloferrocene derivative represented by formula (II) exhibits optical activity. Examples of the haloferrocene are listed below:
(R)-N,N-dimethyl-1-[(S)-2-iodoferrocenyl]ethylamine,
(S)-N,N-dimethyl-1-[(R)-2-iodoferrocenyl]ethylamine,
N-[(R)-1-((S)-2-iodoferrocenyl)ethyl]-N-methylethanolamine,
N-[(R)-1-((S)-2-iodoferrocenyl)ethyl]-(S)-prolinol,
N-[(S)-1-((R)-2-iodoferrocenyl)ethyl]-(S)-prolinol,
N-[(R)-1-((S)-2-iodoferrocenyl)ethyl]-(1S,2R)-ephedrine,
N-[(S)-1-((R)-2-iodoferrocenyl)ethyl]-(1S,2R)-ephedrine,
N-[(R)-1-((S)-2-iodoferrocenyl)ethyl]-(1R,2S)-ephedrine,
N-[(R)-1-((S)-2-iodoferrocenyl)ethyl]-(1S,2R)-norephedrine,
N-[(R)-1-((S)-2-iodoferrocenyl)ethyl]-N-t-butyl-(S)-2-phenylethanolamine,
N-[(S)-1-((R)-2-iodoferrocenyl)ethyl]-N-t-butyl-(S)-2-phenylethanolamine,
N-[(R)-1-((S)-2-iodoferrocenyl)ethyl]-N-t-butyl-(S)-1-phenylethanolamine,
(R)-N,N-dimethyl-1-[(S)-2-bromoferrocenyl]ethylamine,
N-[(R)-1-((S)-2-bromoferrocenyl)ethyl]-(1S,2R)-ephedrine,
N-(2-iodoferrocenyl)methyl-(1S,2R)-ephedrine.

A process for preparation of the derivative represented by formula (II) will be explained below:
(A) Process 1:

The haloferrocene derivative represented by formula (II) is obtained by reacting a ferrocene derivative represented by formula (III):

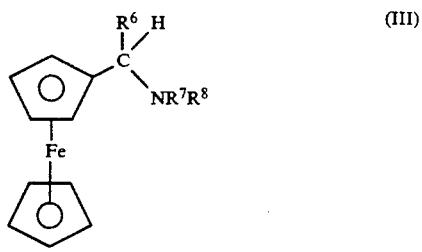

(In the formula, definition of $R^6$, $R^7$ and $R^8$ are the same as those above.) with organic lithium compound to obtain a lithiated compound and then reacting the resulting lithiated compound with halogenation agent.

Examples of the organic lithium compound used for the lithiation include n-butyl lithium, sec-butyl lithium, tert-butyl lithium, methyl lithium and phenyl lithium. An amount of the lithium compound suitably ranges from 0.1 to 2.0 equivalents, preferably from 0.7 to 1.5 equivalents to the ferrocene derivative (III). It is preferred to use these lithium compound in the form of 5 to 30% hexane or ether solution. Further, it is suitable that the lithiation reaction is conducted in the presence of one or more solvent(s), for example ethers such as ethylether and tetrahydrofurane); straight chain hydrocarbons such as pentane, hexane and heptane; or aromatic hydrocarbons such as benzene, toluene, xylene and dichlorobenzene under the following conditions:

Reaction temperature: −30° to 50° C., preferably −10° to 30° C.

Reaction time: 0.1 to 5 hours

Reaction pressure: atmospheric pressure to increased pressure, preferably from 1 to 3 atms Atmosphere: nitrogen or argon The lithiation reaction can also be carried out in accordance with the method reported by Ugi et al. J. Am. Chem. Soc., vol. 92, 5389 (1970).

The halogenation of the lithiation compound is conducted by using a halogenation agent such as iodine, bromine, chlorine, N-iodosuccinimide, N-chlorosuccinimide. The halogenation agent can be added to a reaction mixture as it is or a solution dissolving it in a solvent.

The solvents exemplified as those used for lithiation reaction can be used as the solvent for the halogenation agent and halogenation reaction. An amount of halogenation agent suitably ranges from 0.1 to 2.0 equivalents, preferably from 0.7 to 1.5 equivalents to the ferrocene derivative (III) used in the lithiation reaction. It is preferred to conduct the halogenation reaction under the following conditions:

Reaction temperature: −120° to 0° C., preferably −100° to −30° C.

Reaction time: 0.1 to 10 hours

Reaction pressure: atmospheric pressure to increased pressure, preferably from 1 to 3 atms Atmosphere: nitrogen or argon The progress of the halogenation reaction can be analyzed by thin layer chromatography. At the end of the reaction, the reaction is stopped by addition of water to the reaction system and then the reaction mixture is subjected to extraction with ether. Then the objective compound is collected from the extract solution by column chromatography.

Some of the ferrocene derivatives (III) used as the starting material in the above process 1 are known. (Refer to I. Ugi et al., J. Org. Chem., vol.37, 3052 (1972); Liebigs Ann. Chem., 1986, 251; S. Allenmark et al., Chemica Scripta. Vol, 7, 97 (1975).) On the other hand, compounds represented by formula (II) wherein $R^6$ is hydrogen, an alkyl group, a benzyl group or an aryl group, $R^7$ and $R^8$ are respectively an alkyl group having 2 or more carbon atoms, a benzyl group, an aryl group or unsubstituted or substituted 2-hydroxyethyl group, or $R^7$ and $R^8$ form a heterocyclic ring together with a nitrogen atom are novel. Examples of an alkyl group, a benzyl group, an aryl group and substituted 2-hydroxyethyl group are the same as those mentioned in the explanation of formula (II).

Examples of novel ferrocene derivatives represented by formula (III) are as follows N-[(R)-1-ferrocenylethyl)-N-methyl-2-ethanolamine,
N-[(R)-1-ferrocenylethyl]-(S)-prolinol,
N-[(S)-1-ferrocenylethyl]-(S)-prolinol,
N-[(R)-1-ferrocenylethyl]-(1S,2R)-ephedrine,
N-[(S)-1-ferrocenylethyl]-(1S,2R)-ephedrine,
N-[(R)-1-ferrocenylethyl]-(1S,2R)-norephedrine,
N-(ferrocenylmethyl)-(1S,2R)-ephedrine,
N-[(R)-1-ferrocenylethyl]-N-t-butyl-(S)-2-phenylethanolamine,
N-[(S)-1-ferrocenylethyl]-N-t-butyl-(S)-2-phenylethanolamine.

A novel ferrocene derivative represented by formula (III) can be synthesized by the following method:

A ferrocene derivative (III) wherein $R^7$ and $R^8$ are other than a methyl group can be synthesized by reacting compound (III) wherein $R^7$ and $R^8$ are methyl which is a known one (see J. Am. Chem. Soc., vol.92, 5389 (1970)) with methyl iodide to obtain a quaternary ammonium salt and reacting this salt with a primary or secondary amine derivative or ammonia (refer to I. Ugi et al., J. Org. Chem.. vol.37, 3052 (1972); T. Hayashi et al., Bull. Chem. Soc. Jpn., vol.53, 1138 (1980)).

Reaction with quaternary ammonium salt

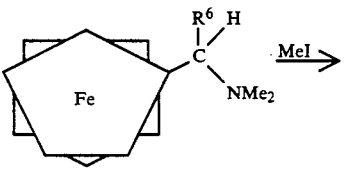

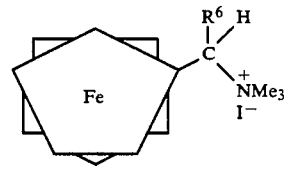

MeI: 0.5 to 40 equivalents

Solvent: ketones such as acetone, methylethylketone, nitriles such as acetonitrile, benzonitrile Temperature: −30° to 80° C., preferably −10° to 40° C.

Time: 0.1 to 5 hours

Pressure: atmospheric to increased pressure, preferably 1 to 3 atms

Atmosphere: nitrogen or argon

Separation: when a product is in the form of crystal, it is separated by filtration. Otherwise, prior to filtration, ethylether or hexane is added to a reaction product to form crystals of the product.

Reaction with amine or ammonia

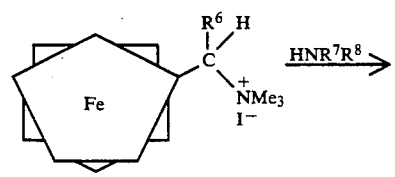

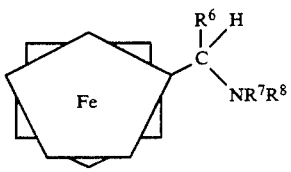

HNR$^7$R$^8$: 1 to 30 equivalents
Solvent: nitriles such as acetonitrile, benzonitrile ethers such as ethylether, tetrahydrofuran
Temperature: 0° to 100° C., preferably 10° to 90° C.
Time: 0.5 to 100 hours
Pressure: atmospheric to increased pressure, preferably 1 to 3 atms
Atmosphere nitrogen or argon
Separation recrystallization or column chromatography (B) Process 2

In accordance with the following scheme, a haloferrocene derivative (II) can be synthesized by applying the method reported in Tetrahedron, 26, 5453 (1970) to a ferrocene derivative represented by formula (III).

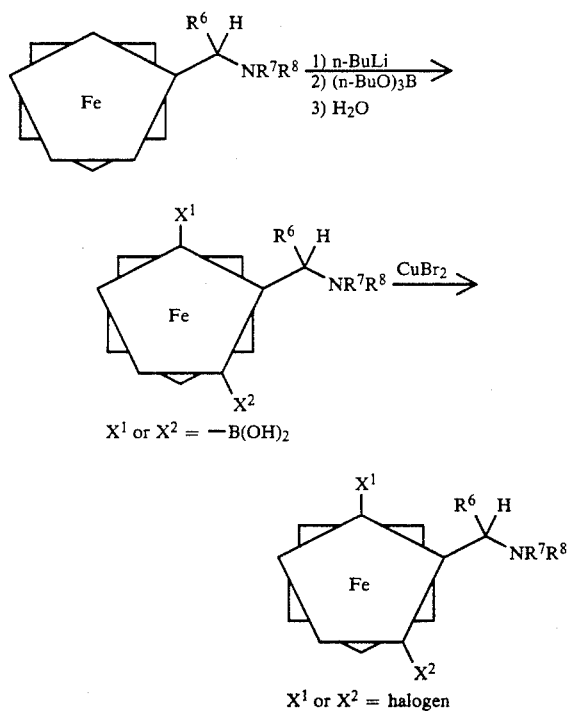

X$^1$ or X$^2$ = halogen

A haloferrocene derivative represented by formula (II) wherein R$^7$ and R$^8$ are other than a methyl group can be synthesized by the method in which a haloferrocene derivative (II) wherein R$^7$ and R$^8$ are methyl groups is reacted with methyl iodide to form a quaternary ammonium salt followed by reaction with primary or secondary amine with appropriate R$^7$ and R$^8$. (Refer to I. Ugi et al., J. Org. Chem., vol.37, 3052 (1972); T. Hayashi et al., Bull. Chem. Soc. Jpn., vol.53, 1138 (1980)).

Since a number of thus obtaining haloferrocene derivatives are crystallized, a small amount of diastereomers (see J.Am.Chem.Soc., vol. 92, 5389(1970)) contained in the product can be removed by recrystallization. Therefore, optically pure ferrocene derivatives (II) and (I) can be obtained.

The compound of the present invention represented by formula (I) can be obtained by lithiation reaction of iodide of haloferrocene derivative (II) which is represented by formula (IV) with n-butyllithium and reaction of the resulting lithiated product with a ketone or aldehyde represented by formula (V) as shown below:

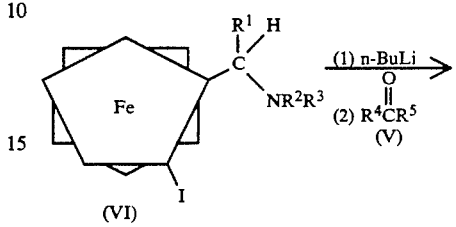

In addition to n-butyl lithium, sec-butyl lithium, t-butyl lithium, methyl lithium and phenyl lithium can be used for lithiation as an organic lithium compound. An amount of the organic lithium compound used in the above reaction ranges from 0.1 to 2.0 equivalents, preferably 0.7 to 1.5 equivalents to ferrocene iodide (IV). It is preferred to use 5 to 30% organic lithium compound solution in hexane or ether. The lithiation reaction is suitably carried out in the presence of a solvent, for example ethers such as ethylether, tetrahydrofuran, straight chain hydrocarbons such as pentane, hexane, heptane, aromatic hydrocarbons such as benzene, toluene, xylene, dichlorobenzene and a mixture of two or more of the above solvents under the following conditions:

Temperature: −30° to 50° C., preferably −10° to 30° C.
Time: 0.1 to 5 hours
Pressure: atmospheric to increased pressure, preferably 1 to 3 atms
Atmosphere: nitrogen or argon The reaction of the lithiated product with the ketone or aldehyde (V) is preferably conducted by addition of a ketone or aldehyde (V) in ether to the reaction mixture An amount of the ketone or aldehyde (V) used in this reaction ranges from 0.1 to 2.0 equivalents, preferably 0.7 to 1.5 equivalents to ferrocene iodide (IV) used in the lithiation. This reaction is suitably carried out under the following conditions:

Temperature: −40° to 70° C., preferably −20° to 40° C.
Time: 1 to 3 hours
Pressure: atmospheric to increased pressure, preferably 1 to 3 atms
Atmosphere: nitrogen or argon The reaction is stopped by addition of an aqueous phosphoric acid solution to the reaction mixture and an aqueous layer is made alkaline. Then the mixture is subjected to extraction with ether and column chromatography to obtain the objective compound represented by formula (I). When compound (V) is an aldehyde, two types of diastereomers are produced by the reaction since a new asymmetric center is generated in the reaction. It is possible to separate these diastereomers from each other by means of chromatography. Since one of the diastereomers has the stable structure it can also be isolated by subjecting the diastereomers to acid treatment to fully isomerize the other diastereomer (see J.Am.Chem.Soc., vol.95, 482(1973)).

The ketone and aldehyde (V) used in the above reaction are commercially available.

Optically active ferrocene derivatives of the present invention can be a useful ligand to metals with Lewis acidity and therefore, it is possible to provide a catalyst exhibiting good enantioselectivity for asymmetric induction using metals with Lewis acidity such as zinc, boron, aluminum, titanium, cerium and nickel.

Further, according to the present invention, chiral ferrocene derivatives having a wide range of substituents are provided and these derivatives can be applied to various asymmetric syntheses. Furthermore, catalysts for asymmetric synthesis applied to heterogeneous system and polymer gel for optical resolution are expected to be provided by use of the chiral ferrocene derivatives of the present invention. (See F. S. Arimoto et al., J.Am.Chem.Soc., Vol.77, 6295(1955); Y. Sasaki et al., J.Polym.Sci., Polym.Chem.Ed., Vol.11, 1213(1973).)

The present invention will now be illustrated on the basis of the following examples but the scope of the present invention is not limited to these examples.

EXAMPLE 1

20.0 g (77.8 mmol) of (R)-N,N-dimethyl-1-ferrocenylethylamine was added under argon atmosphere to a glass vessel (atmospheric pressure use only) with an agitator and dissolved in acetone 37 ml. After cooling with ice water, methyl iodide 21 ml (337 mmol) was added to the vessel and reacted for 15 minutes under cooling with ice water. After reaction, ethylether 160 ml was added to the vessel and crystals were deposited. The crystals were collected by filtration to obtain (R)-N,N,N-trimethyl-1-ferrocenylethylammonium iodide 31.0 g (77.8 mmol) (yield: 100%).

Then, to the resulting quaternary ammonium salt 31.0 g (77.8 mmol), (1S,1R)-norephedrine 58.8 g (388 mmol) and acetonitrile 370 ml were added and reacted at room temperature. After 48 hours, ethylether was added to the reaction mixture and washed with water. The resulting ether solution was dried over anhydrous sodium sulfate and evaporated. The residue was recrystallized from ethyl acetate to obtain N-[(R)-1-ferrocenylethyl-(1S,2R)-norephedrine 25.4 g (70.0 mmol) (yield: 90%).

$[\alpha]_D^{23}$ −65.7° (C 0.530, AcOEt) Melting point: 147° C. 60 MHz $^1$H NMR ($\delta$, CDCl$_3$); 0.82(3H,d,J=6 Hz), 1.40 (3H,d,J=6 Hz), 2.55(2H,br,s), 2.85-3.35(1H,m), 3.60(1H,q,J=7 Hz), 3.95-4.25(m,9H), 4.70(1H,d,J=4 Hz), 7.25(5H,s) IR(KBr) 3450, 3100, 2998, 2890, 1600, 1105, 995, 905, 830, 810, 702 cm$^{-1}$

EXAMPLES 2-4

The procedures of Example 1 were repeated except that N,N-dimethyl-1-ferrocenylethylamines possessing configuration shown in Table 2 were used and amines shown in Table 2 were used in place of norephedrine to obtain ferrocene derivatives listed in Table 2. When the product was liquid, purification was carried out by means of alumina column chromatography. The results were shown in Table 2.

TABLE 2

| Example | Configuration* | —NR$^2$R$^3$ | Product | Yield (%) | Specific rotation | m.p. |
|---|---|---|---|---|---|---|
| 2 | S | (1S,2R)-norephedrine | | 89 | $[\alpha]_D^{20}$ +17.6° (C 0.60, AcOEt) | 97° C. |
| 3 | R | (1s,2R)-ephedrine | | 95 | $[\alpha]_D^{20}$ −50.2° (C 1.14, EtOH) | oil |
| 4 | S | (S)-prolinol | | 93 | $[\alpha]_D^{20}$ +45.1° (C 1.01, EtOH) | oil |

*Configuration of N,N-dimethyl-1-ferrocenylethylamine

SPECTRUM DATA

EXAMPLE 2

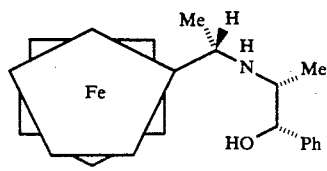

60 MHz $^1$H NMR ($\delta$, CDCl$_3$); 0.80(3H,d,J=7 Hz), 1.42 (3H,d,J=7 Hz), 2.20(2H,br,s), 2.80-3.35(1H,m), 3.78 (1H,q,J=7 Hz), 4.18(9H,s), 4.70(1H,d,J=4 Hz), 7.40(5H,s) IR(KBr) 3350, 3100, 2995, 1600, 1450, 1105, 1000, 819, 710 cm$^{-1}$

EXAMPLE 3

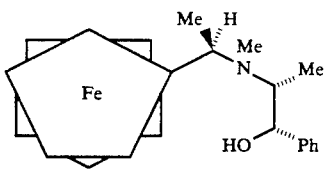

60 MHz $^1$H NMR (δ, CDCl$_3$); 0.70(3H,d,J=7 Hz), 1.43 (3H,d,J=7 Hz),2.01(3H,s), 2.55–3.00(1H,m), 3.21(1H,br,s), 3.80–4.35(10H,m), 4.65(1H,d,J=4 Hz), 7.20(5H,s) IR(neat) 3400, 3100, 2980, 1600, 1450, 1105, 1000, 820, 700 cm$^{-1}$

EXAMPLE 4

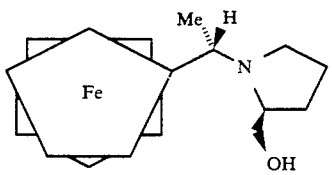

60 MHz $^1$H NMR (δ, CDCl$_3$); 1.45 (3H,d,J=7 Hz), 1.50–2.10(4H,m), 2.30–2.70(3H,m), 2.75–3.40(3H,m), 3.60–3.75(1H,m), 4.20(9H,s) IR(neat) 3400, 3100, 2980, 2870, 1400, 1105, 1000 cm$^{-1}$

EXAMPLE 5

2.66 g (10.3 mmol) of (R)-N,N-dimethyl-1-ferrocenylethylamine was added under argon atmosphere to a 100 ml glass vessel (atmospheric pressure use only) with an agitator and dissolved in ether 25 ml. After cooling with ice water, secondary butyl lithium in cyclohexane 12.4 ml (0.94M, 11.7 mmol) was added dropwise to the vessel and reacted for 1 hour under cooling with ice water. Then the reaction mixture was cooled in a dry ice-acetone bath and iodine (3.00 g, 11.7 mmol) in tetrahydrofuran 25 ml was added dropwise. After 1 hour under cooling, water was added to the vessel to stop the reaction and the aqueous layer was made alkaline. The resulting solution was subjected to extraction with ether and the organic layer was dried over anhydrous sodium sulfate and evaporated. The residue was Purified by alumina column chromatography to obtain (R)-N,N-dimethyl-1-[(S)-2-iodoferrocenyl]ethylamine 3.12 g (yield:

This was recrystallized from acetonitrile.

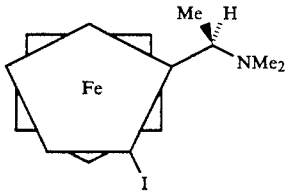

$[\alpha]_D^{22} = -9.32°$ (C 1.01, EtOH) m.p. 78°–79° C. 60 MHz $^1$H NMR (δ, CDCl$_3$); 1.50(3H,d,J=8.0 Hz), 2.15(6H,s), 3.15(1H,q,J=7.5 Hz), 4.13(7H,s), 4.40–4.60(1H,m) IR(KBr) 3100, 2970, 2940, 2802, 2760, 1100, 10000 cm$^{-1}$

EXAMPLES 6–10

The procedures of Example 5 were repeated excepting that solvents and halogenation agents listed in Table 3 were used. The results were shown in Table 3 below.

TABLE 3

| Example | Solvent | Halogenation agent | Yield (%) |
|---|---|---|---|
| 6 | ether | Br$_2$ | 33 |
| 7 | ether | NBS[1] | 10 |
| 8 | ether-THF | NBS[1] | 52 |
| 9 | ether | I$_2$ | 63 |
| 10 | ether-THF | NIS[2] | 53 |

[1]NBS: N-bromosuccinimide
[2]NIS: N-iodosuccinimide

EXAMPLES 11–14

The procedures of Example 5 were repeated except that starting materials listed in Table 4 were used in place of (R)-N,N-dimethyl-1-ferrocenylethylamine, 24.8 ml of secondary butyl lithium in cyclohexane was used and ethyl acetate was used as the recrystallization solvent. The results were listed in Table 4.

TABLE 4

| Example | Starting material | Product | Yield (%) | Specific rotation | m.p. (°C.) |
|---|---|---|---|---|---|
| 11 | | | 55 | $[\alpha]_D^{20}$ −37.1° (c1.05, EtOH) | 90 |
| 12 | | | 46 | $[60]_D^{22}$ −21.9° (c0.42, AcOEt) | 157 |

TABLE 4-continued

| Example | Starting material | Product | Yield (%) | Specific rotation | m.p. (°C.) |
|---|---|---|---|---|---|
| 13 | (ferrocenyl-CH(Me)-pyrrolidine-2-CH2OH) | (iodo-ferrocenyl-CH(Me)-pyrrolidine-2-CH2OH) | 52 | $[\alpha]_D^{20}$ +30.3° (c0.578, AcOEt) | 112 |
| 14 | (ferrocenyl-CH(Me)-N(Me)-CH(Ph)-CH(OH)) | (iodo-ferrocenyl-CH(Me)-N(Me)-CH(Ph)-CH(OH)) | 50 | $[\alpha]_D^{20}$ −20.9° (c1.246, EtOH) | oil |

EXAMPLE 11

60 MHz $^1$H NMR ($\delta$, CDCl$_3$): 1.40(3H,d,J=7.0 Hz), 2.10(3H,s), 2.53(2H,t J=5.0 Hz), 2.70(1H,s), 3.50(2H,t,J=5.0 Hz), 3.90 (1H,q,J=7.0 Hz), 4.11(5H,s), 4.16–4.31(2H,m), 4.42–4.61(1H,m) IR(KBr) 3450, 3098, 2950, 2890, 1105, 1000 cm$^{-1}$

EXAMPLE 12

400 MHz $^1$H NMR ($\delta$, CDCl$_3$); 1.44(3H,br), 1.58(2H,br), 1.72–1.88(2H,m), 2.43(1H,br), 2.52(1H,br), 2.80(1H,s), 3.01(1H,br), 3.29(1H,br), 3.71(1H,br), 3.98(1H,q,J=8.0 Hz), 4.12(5H,s), 4.17–4.47(4H,m) IR(KBr) 3450, 3098, 2960, 1102, 1000 cm$^{-1}$

EXAMPLE 13

400 MHz $^1$H NMR ($\delta$, CDCl$_3$); 1.57(3H,br), 1.50–1.78(4H,m), 2.60(2H,br), 2.90–3.18(3H,br), 3.98(1H,br), 4.12(5H,s), 4.15–4.30(3H,m) IR(KBr) 3450, 3100, 2970, 1105, 1000 cm$^{-1}$

EXAMPLE 14

60 MHz $^1$H NMR ($\delta$, CDCl$_3$); 0.98(3H,d,J=7.0 Hz), 1.37 (3H,d,J=7.0 Hz), 2.12(3H,s), 2.60–3.12(1H,m), 3.57(1H,s), 4.12(5H,s), 4.23–4.27(3H,m), 4.67–4.72(1H,m), 7.30(5H,s) IR(neat) 3450, 3100, 3070, 2995, 1608, 1108, 1000, 940, 820, 755, 700 cm$^{-1}$

EXAMPLE 15

3.83 g (10.0 mmol) of (R)-N,N-dimethyl-1-[(S)-2-iodoferrocenyl]ethylamine was added under argon atmosphere to a glass vessel (atmospheric pressure use only) with an agitator and dissolved in acetone 20 ml. Methyl iodide 2.86 ml (46 mmol) was added to the vessel and reacted for 10 minutes at room temperature After reaction, ethylether 100 ml was added to the vessel and crystals were precipitated. The crystals were collected by filtration to obtain the quaternary ammonium salt 5.25 g (10.0 mmol).

Then the resulting quaternary ammonium salt was dissolved in acetonitrile 130 ml. Diethylamine 26 ml (250 mmol) was added to this solution and the reaction mixture was stirred at 30° C. for 48 hours. Ethylether was added to the reaction mixture and washed with water. The resulting ether solution was dried over anhydrous sodium sulfate and evaporated. The residue was recrystallized from ethyl alcohol to obtain (R)-N,N-diethyl-1-[(S)-2-iodoferrocenyl]ethylamine 3.70 g (9.0 mmol)(yield: 90%).

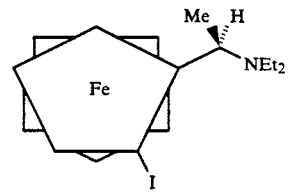

$[\alpha]_D^{27}$ −58.6° (C 0.596, EtOH) Melting point: 49° C. 90 MHz $^1$H NMR ($\delta$, CDCl$_3$); 0.98(6H,t,J=7.2 Hz), 1.39 (3H,d,J=6.6 Hz), 2.39 (2H,q,J=6.9 Hz), 2.42 (2H,q,J=6.9 Hz), 3.90 (1H, q,J=6.6 Hz), 4.09 (5H,s), 4.15–4.21(2H,m), 4.38–4.44(1H,m) IR (KBr) 3100, 2980, 2820, 1104, 1001, 820 cm$^{-1}$

EXAMPLES 16-17

In accordance with the procedures of Example 15 except that amines listed in Table 5 were used instead of diethylamine, the products shown in Table 5 were obtained Product of Example 16

90 MHz $^1$H NMR ($\delta$, CDCl$_3$); 1.16–1.50(6H,m), 1.50(3H,d, J=6.3 Hz), 2.36 (3H,t,J=5.1 Hz), 3.70 (1H,q,J=7.2 Hz), 4.10 (5H,s), 4.16–4.25(2H,m), 4.39–4.49(1H,m) IR (KBr) 3100, 2950, 2860, 2805, 2760, 1108, 1002, 820 cm$^{-1}$ Product of Example 17

90 MHz $^1$H NMR ($\delta$, CDCl$_3$); 0.96(6H,d,J=6.0 Hz), 1.06 (6H,d,J=6.0 Hz), 1.49 (3H,d,J=6.3 Hz), 2.89–3.37(2H,m), 4.03(1H,q,J=6.6 Hz), 4.06(5H,s), 4.10–4.28(2H,m), 4.36–4.45(1H,m) IR (KBr) 3105, 2995, 2898, 1365, 1195, 1109, 1002, 820 cm$^{-1}$

TABLE 5

| Example | Amine | Product | Yield (%) | Specific rotation | m.p. (°C.) |
|---|---|---|---|---|---|
| 16 | (piperidine structure, HN) | (ferrocene with Me H, N-piperidino, I) | 90 | $[\alpha]_D^{26}$ −21.9° (C 0.960, EtOH) | 67 |
| 17 | HN(i-Pr)$_2$ | (ferrocene with Me H, N(i-Pr)$_2$, I) | 80 | $[\alpha]_D^{26}$ −77.6° (C 1.08, EtOH) | 58–60 |

EXAMPLE 18

2.12 g (5.0 mmol) of (R)-1-[(S)-2-iodoferrocenyl]-1-(1-piperidino)ethane obtained in Example 16 was added under argon atmosphere to a glass vessel (atmospheric pressure use only) with an agitator and dissolved in ethylether 12 ml. After cooling with ice water, n-butyl lithium in hexane 3.13 ml (1.60M, 5.0 mmol) was added dropwise to the vessel and reacted for 5 minutes under cooling with ice water. Then, benzophenone 911 mg (50 mmol) in ether 15 ml was added to the reaction mixture and stirred at room temperature for 1 hour 8 % aqueous phosphoric acid solution was added to the mixture to stop the reaction. The resulting acid solution was washed with ethylether and treated with a conc. aqueous alkaline solution to make it alkaline. Thus obtained alkaline solution was subjected to extraction with ethylether and the ethylether solution was dried over anhydrous sodium sulfate The solvent was evaporated and the residue was purified by alumina column chromatography (hexane:AcOEt) to obtain (R)-1-[(S)-2-diphenylhydroxymethyl-ferrocenyl]-1-(1-piperidino)ethane 1.80 g (3.75 mmol, yield 75%).

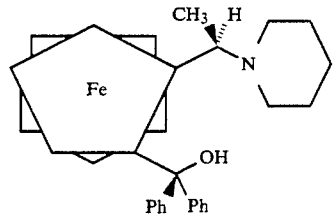

$[\alpha]_D^{21}$ −209.9 ° (C 0.490, EtOH) Melting point: 62°–69° C. 90 MHz $^1$H NMR (δ, CDCl$_3$); 0.29–1.70 (6H,m), 1.24 (3H,d,J=6.3 Hz), 2.25 (4H,t,J=5.7 Hz), 3.80 (5H,s), 3.89–4.01(1H,m), 4.03–4.20(1H,m), 4.20–4.37(1H,m), 4.40(1H,q,J=6.9 Hz), 6.98–7.45(8H,m), 7.50–7.75(2H,m), 8.72(1H,s,OH) IR (KBr) 3460, 3100, 3070, 2950, 2840, 1600, 1444, 1104, 1002, 820, 762, 753, 703 cm$^{-1}$

EXAMPLES 19–23

According to the procedures of Example 18 except that ferrocene derivatives listed in Table 6 were used in place of (R)-1-[(S)-2-iodoferrocenyl]-1-(1-piperidino)ethane and ketones listed in Table 6 were used in place of benzophenone, the products shown in Table 6 were obtained.

TABLE 6

| Example | Starting material | | Product | Yield (%) | Specific rotation | m.p. (°C.) |
|---|---|---|---|---|---|---|
| 19 | (ferrocene with Me H, NMe$_2$, I) | (isopropyl methyl ketone) | (ferrocene with Me H, NMe$_2$, C(OH)(iPr)$_2$ group) | 40 | $[\alpha]_D^{27}$ +50.8° (c 0.634, EtOH) | 60–61 |

TABLE 6-continued

| Example | Starting material | Product | Yield (%) | Specific rotation | m.p. (°C.) |
|---|---|---|---|---|---|
| 20 | Ferrocene with Me H, NMe₂ substituent and I; cyclohexanone | Ferrocene with Me H, NMe₂ and C(OH)(cyclohexyl) | 50 | $[\alpha]_D^{27}$ −17.3° (c 0.550, EtOH) | 108 |
| 21 | Ferrocene with Me H, NEt₂ and I; PhC(O)Ph | Ferrocene with Me H, NEt₂ and C(OH)Ph₂ | 65 | $[\alpha]_D^{26}$ −229.5° (c 0.346, EtOH) | 48–50 |
| 22 | Ferrocene with Me H, piperidino and I; anthrone | Ferrocene with Me H, piperidino and 9-(OH)-9,10-dihydroanthracenyl | 43 | $[\alpha]_D^{26}$ −190.6° (C 0.770, EtOH) | 90–93 |
| 23 | Ferrocene with Me H, N(i-Pr)₂ and I; PhC(O)Ph | Ferrocene with Me H, N(i-Pr)₂ and C(OH)Ph₂ | 52 | $[\alpha]_D^{25}$ −192.0° (C 0.762, EtOH) | 50–53 |

Product of Example 19
90 MHz ¹H NMR (δ, CDCl₃); 0.37(3H,d,J=6.6 Hz), 0.85 (3H,d,J=6.3 Hz), 1.29 (6H,d,J=6.6 Hz), 1.45 (3H,d,J=6.6 Hz), 1.60–1.97 (1H,m), 2.10 (6H,s), 2.30–2.68(1H,m), 3.78–3.95 (1H,m), 4.09(5H,s), 4.11–4.23(3H,m), 7.69(1H,s,−OH) IR (KBr) 3420, 3100, 2998. 2898. 2800, 1108, 1004, 828, 820 cm⁻¹

Product of Example 20
90 MHz ¹H NMR (δ, CDCl₃); 1.21(3H,d,J=6.3 Hz), 1.30–2.42 (10H,m), 2.09(6H,s), 3.90–4.09(3H,m), 4.12(5H,s), 4.29 (1H,q, J=6.3 Hz), 7.18(1H,s,−OH) IR (KBr) 3450, 3100, 2950, 2800, 1105, 822 cm⁻¹

Product of Example 21
90 MHz ¹H NMR (δ,CDCl₃); 0.63(6H,t,J=7.2 Hz), 1.20 (3H,d, J=6.0 Hz), 1.89–2.58(4H,m), 3.78 (5H,s), 3.89–4.03(1H,m), 4.07–4.20(1H,m), 4.20–4.31(1H,m), 4.65(1H,q,J=6.9 Hz), 6.98–7.48(8H,m), 7.53–7.76(2H,m) 8.70(1H,s,−OH) IR (KBr) 3450, 3100, 3060, 2995, 2860, 1598, 1109, 1003, 820, 755, 702 cm⁻¹

Product of Example 22
90 MHz ¹H NMR (δ, CDCl₃); 1.32(3H,d,J=6.0 Hz), 1.35–1.95(6H, m), 2.64(4H,t,J=5.4 Hz), 3.20–3.39(1H,m), 3.50(5H,s), 3.70–3.90(1H,m), 3.90–4.02(1H,m), 4.02–4.18(1H,m), 4.20–4.60(2H, m), 7.06–7.50(4H,m), 7.60–7.83(1H,m), 7.89–8.09(1H,m) IR (KBr) 3460, 3100, 3150, 2950, 2830, 1108, 1001, 820,760, 747 cm⁻¹

Product of Example 23
90 MHz ¹H NMR (δ, CDCl₃); 0.69(6H,d,J=6.0 Hz), 1.09(6H,d, J=6.0 Hz), 1.38(3H,d,J=6.3 Hz), 2.85–3.22(2H,m), 3.70(5H,s), 3.90–4.10(1H,m), 4.10–4.23(1H,m), 4.23–4.37(1H,m), 4.82 (1H,q,J=6.9 Hz), 6.98–7.47(8H,m), 7.60–7.83(2H,m), 8.45(1H,s,−OH) IR (KBr) 3450, 3100 3070, 2990, 2890, 1600, 1105, 1000, 819, 750, 700 cm⁻¹

EXAMPLES 24–26

The procedures of Example 18 were repeated except that ferrocene derivatives listed in Table 7 were used in place of (R)-1-[(S)-2-iodoferrocenyl]-1-(1-piperidino)ethane and aldehydes listed in Table 7 were used in place of benzophenone as a carbonyl compound. The products of these examples contained two diastereomers. These diastereomers were separated by means of chromatography using alumina or silica gel, and physical properties of each diastereomer were measured and shown in Table 7.

TABLE 7

| Example | Starting material | Product | Yield (%) | Specific rotation (C, solvent) product 1 | Specific rotation (C, solvent) product 2 | m.p. (°C) product 1 | m.p. (°C) product 2 |
|---|---|---|---|---|---|---|---|
| 24 | (ferrocene with Me, H, NMe₂, I) PhCHO | (ferrocene with Me, H, NMe₂, OH, Ph, H) | 65 | $[\alpha]_D^{27}$ −120.6° (C 1.04, EtOH) | $[\alpha]_D^{24}$ −92.0° (C 0.766, EtOH) | oil | oil |
| 25 | (ferrocene with Me, H, NMe₂, I) t-BuCHO | (ferrocene with Me, H, NMe₂, OH, t-Bu, H) | 73 | $[\alpha]_D^{26}$ −44.2° (C 0.606, EtOH) | $[\alpha]_D^{26}$ +130.2° (C 0.765, EtOH) | 121–124 | 91 |
| 26 | (ferrocene with Me, H, N-piperidino, I) t-BuCHO | (ferrocene with Me, H, N-piperidino, OH, t-Bu, H) | 60 | $[\alpha]_D^{28}$ −30.8° (C 0.120, EtOH) | $[\alpha]_D^{28}$ +131.2° (C 0.128, EtOH) | oil | oil |

EXAMPLE 24

Product 1

90 MHz $^1$H NMR (δ, CDCl$_3$); 1.36(3H,d,J=6.6 Hz), 2.22(6H,s), 3.38–3.58(1H,m), 3.80–4.40(3H,m), 4.03(5H,s), 5.94(1H,s), 7.12–7.68(5H,m), 7.70–8.02(1H,s,OH) IR (neat) 3102, 3049, 2998, 2849, 2800, 1605, 1105, 1000, 819, 738, 700 cm$^{-1}$ Product 2

90 MHz $^1$H NMR (δ, CDCl$_3$); 1.23(3H,d,J=6.0 Hz), 2.19(6H,s), 3.80(5H,s), 3.90–4.35(4H,m), 5.47(1H,s), 6.00–6.70(1H,−OH), 7.09–7.68(5H,m) IR (neat) 3370, 3100, 3040, 2998, 2798, 1600, 1104, 1000, 818, 719, 700 cm$^{-1}$

EXAMPLE 25

Product 1

90 MHz $^1$H NMR (δ, CDCl$_3$); 0.94(9H,s), 1.29(3H, d,J=6.6 Hz), 2.07(6H,s), 2.62(1H,−OH), 3 80(1H,q,J=7 5 Hz), 3.97–4.25 (3H,m), 4.16(5H,s), 4.25–4.35(1H,m) IR (KBr) 3480, 3105, 2999, 2970, 2840, 2800, 1106, 1002, 818 cm$^{-1}$

Product 2

90 MHz $^1$H NMR (δ, CDCl$_3$); 1.18(9H,s), 1.29(3H,d,J=6.0 Hz), 2.15(6H,s), 4.00(5H,s), 4.05–4.18(3H,m), 4.19–4.34(1H,m), 4.52(1H,s), 7.60(1H,−OH) IR (KBr) 3450, 3102, 3000, 2960, 2850, 2800, 1108, 1005, 820 cm$^{-1}$

EXAMPLE 26

Product 1

90 MHz $^1$H NMR (δ, CDCl$_3$); 0.99(9H,s), 1.27(3H, d,J=5.4 Hz), 1.18–1.55(6H,m), 2.20–2.60(4H,m), 3.79(1H,q,J=7.2 Hz), 3.97–4.37(4H,m), 4.11(5H,s) IR (neat) 3100, 3000, 2950, 2820, 1105, 1000, 820 cm$^{-1}$ Product 2

90 MHz $^1$H NMR (δ, CDCl$_3$); 1.20(9H,s), 1.33(3H,d,J=6.00 Hz), 1.29–1.56(6H,m), 2.32–2.57(4H,m), 4.00(5H,s), 4.03–4.20 (3H,m), 4.20–4.37(1H,m), 4.50(1H,s) IR (neat 3250, 3105, 3000, 2960, 2840, 1112, 1009, 822 cm$^{-1}$

EXAMPLES 27–28

The procedures of Example 18 were repeated except that (R)-N,N-dimethyl-1-[(S)-2-iodoferrocenyl]ethylamine was used in place of (R)-1-[(S)-2-iodoferrocenyl]-1-(1-piperidino)ethane and aldehydes listed in Table 8 were used in place of benzophenone as a carbonyl compound. Products of these examples contained two diastereomers and these diastereomers were separated by means of chromatography using alumina or silica gel. Physical properties of each diastereomer separated were measured and shown in Table 8.

EXAMPLE 27

Product 1

90 MHz $^1$H NMR (δ, CDCl$_3$); 1.30(3H,d,J=6.6 Hz), 2.07(6H,s), 2.24(3H,s), 2.43(6H,s), 3.78–3.95(1H,m), 3.95–4.30(3H,m), 4.15(5H,s), 6.06(1H,s), 6.77(2H,s) IR (KBr) 3450, 3100, 3000, 2980, 2840, 2800, 1610, 1464, 1319, 1107, 1000, 950, 812, 785, 737, 700 cm$^{-1}$

Product 2

90 MHz $^1$H NMR (δ, CDCl$_3$); 1.38(3H,d,J=6.8 Hz), 2.21(6H,s), 2.27(3H,s), 2.38(6H,s), 3.57–3.75(1H,m), 3.93(1H,m, J=2.6 Hz), 4.03(5H,s), 4.10–4.23(1H,m), 4.20(1H,q,J=6.8 Hz), 6.53(1H,s), 6.82(1H,s), 8.28(1H,OH) IR (KBr) 3450, 3100, 2999, 2950, 2850, 2800, 1610, 1460, 1370, 1182, 1109, 1072, 1043, 1003, 950, 938, 818, 770, 735, 680 cm$^{-1}$

EXAMPLE 28

Product 1

90 MHz $^1$H NMR ($\delta$, CDCl$_3$); 1.35(3H,d,J=6.8 Hz), 2.27(6H,s), 3.52-3.65(1H,m), 3.87-3.99(1H,m), 3.97(5H,s), 4.15-4.24 (1H,m), 4.47(1H,q,J=6.8 Hz), 6.05(1H,OH), 7.17(1H,s), 7.30-7.60(4H,m), 7.88-8.10(2H,m), 8.40(1H,s), 8.85-9.10(2H,m) IR (KBr) 3440, 3100, 3050, 2970, 2940, 2815, 2775, 1620, 1520, 1365, 1260, 1104, 1040, 1000, 880, 732 cm$^{-1}$ Product 2

90 MHz $^1$H NMR ($\delta$, CDCl$_3$); 1.47(3H,d,J=6.8 Hz, 2.34(6H,s), 3.30-3.42(1H,m), 3.83(5H,s), 4.04-4.16(1H,m), 4.18-4.30 (1H,m), 4.51(1H,q,J=6.8 Hz), 7.25-7.53(4H,m), 7.55(1H,s), 7.89-8.10(2H,m), 8.44(1H,s), 8.60-8.90(2H,m) IR (KBr) 3440, 3100, 2990, 2930, 2785, 1600, 1510, 1350, 1265, 1108, 1035, 1005, 880, 730 cm$^{-1}$

EXAMPLES 29-30

The procedures of Example 18 were repeated except that (R)-N,N-dimethyl-1-[(S)-2-iodoferrocenyl]ethylamine was used in place of (R)-1-[(S)-2-iodoferrocenyl]-1-(1-piperidino)ethane, aldehydes listed in Table 9 were used in place of benzophenone as a carbonyl compound, and reactions were stopped by addition of 8% aqueous phosphoric acid solution and the acid solution was allowed to stand for 0.1 to 4 hours at room temperature. Products were completely isomerized to diastereomers listed in Table 9 by this treatment. Physical properties of the diastereomers were shown in Table 9.

EXAMPLE 29

90 MHz $^1$H NMR ($\delta$, CDCl$_3$); 1.35(3H,d,J=6.6 Hz), 2.20(6H,s), 3.78(6H,s), 3.70-4.00(2H,m), 3.93(5H,s), 4.02-4.20 (1H,m), 4.30(1H,q,J=7.0 Hz), 6.58(1H,s), 6.68(2H,d,J=3.3 Hz), 7.23(1H,d-d,J=8.4 Hz,J=7.0 Hz) IR (KBr) 3450, 3100, 2998, 2950, 2848, 2800, 1595, 1475, 1245, 1180, 1100, 1004, 920, 808, 730 cm$^{-1}$

EXAMPLE 30

90 MHz $^1$H NMR ($\delta$, CDCl$_3$); 1.30(3H,d,J=6.8 Hz), 2.19(6H,s), 3.58-3.73(1H,m), 3.92(1H,t,J=2.6 Hz), 4.03(5H,s), 4.04-4.22 (4H,m), 4.27(5H,s), 4.28-4.45(2H,m), 5.67(1H,s), 7.30(1H,OH) IR (KBr) 3450, 3100, 2995, 2950, 2840, 2800, 1500, 1460, 1368, 1290, 1042, 1005, 1000, 935, 815, 770, 740 cm$^{-1}$

TABLE 8

| Example | Aldehyde | Product | Yield (%) | Specific rotation | m.p. (°C.) |
|---|---|---|---|---|---|
| 27 | Me-substituted benzaldehyde (Me, Me, CHO, Me) | Ferrocene derivative with NMe$_2$ and OH-mesityl groups | 70 | Product 1 $[\alpha]_D^{22}$ +109.6° (C 0.356, EtOH) | 136-139 |
|  |  |  |  | Product 2 $[\alpha]_D^{20}$ −135.2° (C 0.398, EtOH) | 54-57 |
| 28 | 9-anthracenecarboxaldehyde | Ferrocene derivative with NMe$_2$ and OH-anthracenyl groups | 58 | Product 1 $[\alpha]_D^{20}$ −51.3° (C 0.372, EtOH) | 60-62 |
|  |  |  |  | Product 2 $[\alpha]_D^{20}$ +64.8° (C 0.276, EtOH) | 98-103 |

TABLE 9

| Example | Aldehyde | Product | Yield (%) | Specific rotation | m.p. (°C.) |
|---|---|---|---|---|---|
| 29 | 2,6-dimethoxybenzaldehyde (OMe, CHO, OMe) | Ferrocene derivative with NMe$_2$ and OH-(2,6-dimethoxyphenyl) groups | 50 | $[\alpha]_D$ −51.7° (C 0.704, EtOH) | 45-47 |

TABLE 9-continued

| Example | Aldehyde | Product | Yield (%) | Specific rotation | m.p. (°C.) |
|---|---|---|---|---|---|
| 30 | (ferrocene-CHO) | (ferrocene product with Me, H, NMe$_2$, OH, H, Fe) | 45 | $[\alpha]_D$ +45.2° (C 0.354, EtOH) | 65–68 |

What we claim is:

1. A ferrocene derivative with chirality represented by the following formula (I):

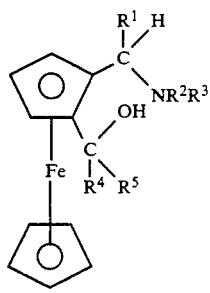

wherein $R^1$ represents an alkyl group, $R^2$ and $R^3$ respectively represent an alkyl group, an aryl group or a benzyl group, or $NR^2R^3$ together form a heterocyclic ring in which $R^2R^3$ represents a hydrocarbon chain having 4 to 6 carbon atoms, $R^4$ and $R^5$ are the same or different and represent hydrogen, a lower alkyl group having 2 to 6 carbon atoms, an aryl group, an anthracenyl group or a ferrocenyl group, or $R^4$ and $R^5$ form a cycloalkyl group having 5 to 7 carbon atoms or a 9-(10-hydroanthracenyl) group together with a carbon atom to which $R^4$ and $R^5$ bond, wherein $R^4$ and $R^5$ are not hydrogen at the same time, and when $R^1$, $R^2$ and $R^3$ are methyl groups, $R^4$ and $R^5$ are not phenyl groups at the same time and are not respectively p-methoxyphenyl and hydrogen.

2. A ferrocene derivative of claim 1 wherein $R^2$ and $R^3$ form a pyrrolidino group together with the nitrogen atom to which $R^2$ and $R^3$ bond.

3. A ferrocene derivative of claim 1 wherein $R^1$ represents a methyl group.

4. A ferrocene derivative of claim 1 wherein $R^2$ and $R^3$ represent a lower alkyl group having 1 to 3 carbon atoms.

5. A ferrocene derivative of claim 1 wherein $R^2$ and $R^3$ form a piperidino group together with a nitrogen atom to which $R^2$ and $R^3$ bond.

6. A ferrocene derivative of claim 1 wherein $R^1$ represents a lower alkyl group having 1 to 6 carbon atoms, $R^2$ and $R^3$ are the same or different and represent a lower alkyl group having 1 to 6 carbon atoms, a phenyl group or a benzyl group.

* * * * *

UNITED STATES PATENT AND TRADEMARK OFFICE
CERTIFICATE OF CORRECTION

PATENT NO. : 5,212,311
DATED : May 18, 1993
INVENTOR(S) : Makoto WATANABE et al.

It is certified that error appears in the above-identified patent and that said Letters Patent is hereby corrected as shown below:

Col. 2, line 37, change "anthracenyl" to --9-(10-hydroanthracenyl)--.
Col. 8, line 20, change "$R^6$" in formula (I) to --$R^1$--.
Col. 10, Table 2 Change formula of product of Example 3 from 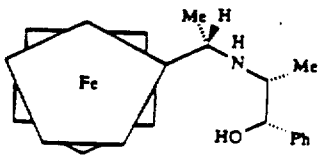

"

to 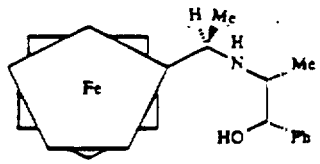

Col. 10, Table 2 change "(1s,2R)-ephedrine" of Example 3 to
--(1S,2R)-ephedrine--.

UNITED STATES PATENT AND TRADEMARK OFFICE
CERTIFICATE OF CORRECTION

PATENT NO. : 5,212,311

DATED : May 18, 1993

INVENTOR(S) : Makoto WATANABE et al.

It is certified that error appears in the above-indentified patent and that said Letters Patent is hereby corrected as shown below:

Col. 12, line 6, change "(yield:" to --(yield: 79%)--.
Col. 13, Table 4 Change formula of starting material from 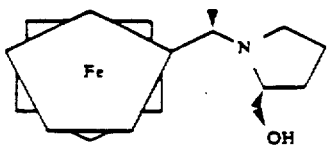

"

to 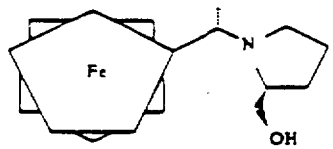

Signed and Sealed this

Fifth Day of July, 1994

Attest:

BRUCE LEHMAN

*Attesting Officer*     *Commissioner of Patents and Trademarks*